United States Patent
Lindner et al.

(10) Patent No.: US 8,648,322 B2
(45) Date of Patent: Feb. 11, 2014

(54) OPTICAL SENSING IN AN ADVERSE ENVIRONMENT

(75) Inventors: Frederick H Lindner, Aesch (CH); Jacob Y. Wong, Goleta, CA (US)

(73) Assignee: Cummins Inc., Columbus, IN (US)

( * ) Notice: Subject to any disclaimer, the term of this patent is extended or adjusted under 35 U.S.C. 154(b) by 172 days.

(21) Appl. No.: 13/019,482

(22) Filed: Feb. 2, 2011

(65) Prior Publication Data

US 2011/0185786 A1  Aug. 4, 2011

Related U.S. Application Data (63) Continuation of application No. 12/818,817, filed on Jun. 18, 2010, now abandoned, which is a continuation of application No. 12/610,800, filed on Nov. 2, 2009, now abandoned.

(60) Provisional application No. 61/197,898, filed on Oct. 31, 2008.

(51) Int. Cl.
*G01N 15/06* (2006.01)
*G01N 21/49* (2006.01)
*G01N 21/85* (2006.01)

(52) U.S. Cl.
USPC ..................... 250/573; 73/35.07

(58) Field of Classification Search
USPC ............... 250/573, 574, 239, 554, 227.23; 356/43, 44, 45, 333, 219, 256; 73/431, 73/35.07, 116, 117.2, 117.3, 35.14, 35.16
See application file for complete search history.

(56) References Cited

U.S. PATENT DOCUMENTS

| | | |
|---|---|---|
| 4,578,762 A | 3/1986 | Wong |
| 4,694,173 A | 9/1987 | Wong |
| 4,756,622 A | 7/1988 | Wong |
| 4,795,240 A | 1/1989 | Wong |
| 4,850,697 A | 7/1989 | Schoennauer |
| 4,924,095 A | 5/1990 | Swanson |
| 5,241,367 A | 8/1993 | Grob et al. |
| 5,464,982 A | 11/1995 | Drucker et al. |
| 5,464,983 A | 11/1995 | Wang |
| 5,583,339 A | 12/1996 | Black et al. |
| 5,617,720 A | 4/1997 | Achleitner et al. |
| 5,748,311 A | 5/1998 | Hamann |
| 5,767,776 A | 6/1998 | Wong |
| 5,798,700 A | 8/1998 | Wong |
| 5,834,777 A | 11/1998 | Wong |
| 5,889,199 A | 3/1999 | Wong |
| 5,894,373 A | 4/1999 | Wong |
| 5,945,924 A | 8/1999 | Marman |
| 5,966,077 A | 10/1999 | Wong |
| 6,029,442 A | 2/2000 | Caren et al. |
| 6,047,543 A | 4/2000 | Caren et al. |

(Continued)

*Primary Examiner* — Francis M Legasse, Jr.
(74) *Attorney, Agent, or Firm* — Krieg DeVault LLP (57) ABSTRACT

A system capable of flowing gases including combustion byproducts past an exposed face of an optical element in an engine fluid conduit, and depositing debris on the exposed face of the optical element. The debris may be soot, unburned hydrocarbons, sulfates, and/or a reductant precipitate. The system is further capable of passing electromagnetic (EM) radiation through the optical element and the flowing gases and interrogating the EM radiation after passing through the optical element and the flowing gases to determine an amount of debris accumulated on the exposed face of the optical element. The system is further capable of heating an electric heating element thermally coupled to the optical element sufficiently to remove accumulated debris from the exposed face in response to the amount of debris exceeding a threshold.

19 Claims, 4 Drawing Sheets

(56) References Cited

U.S. PATENT DOCUMENTS

| | | | |
|---|---|---|---|
| 6,048,500 A | 4/2000 | Caren et al. | |
| 6,107,925 A | 8/2000 | Wong | |
| 6,166,647 A | 12/2000 | Wong | |
| 6,237,575 B1 | 5/2001 | Lampert et al. | |
| 6,253,544 B1 | 7/2001 | Miller et al. | |
| 6,264,899 B1 | 7/2001 | Caren et al. | |
| 6,321,531 B1 | 11/2001 | Caren et al. | |
| 6,330,794 B1 | 12/2001 | Caren et al. | |
| 6,344,798 B1 | 2/2002 | Schell | |
| 6,357,223 B1 | 3/2002 | Caren et al. | |
| 6,810,660 B2 | 11/2004 | Hepburn et al. | |
| 6,810,718 B2 | 11/2004 | Wilson | |
| 6,842,243 B2 | 1/2005 | Tokhtuev et al. | |
| 6,917,038 B2 | 7/2005 | Zheng et al. | |
| 6,982,431 B2 | 1/2006 | Modlin et al. | |
| 7,007,547 B2 * | 3/2006 | Philipp et al. | 73/114.09 |
| 7,084,963 B2 | 8/2006 | Leipertz | |
| 7,176,460 B1 | 2/2007 | Wong | |
| 7,178,331 B2 | 2/2007 | Blakeman et al. | |
| 7,186,979 B1 | 3/2007 | Wong | |
| 7,214,939 B1 | 5/2007 | Wong | |
| 7,240,482 B2 | 7/2007 | Hepburn et al. | |
| 7,264,785 B2 | 9/2007 | Blakeman et al. | |
| 7,313,911 B2 | 1/2008 | Pfeifer et al. | |
| 7,409,823 B2 | 8/2008 | Price et al. | |
| 7,480,044 B2 | 1/2009 | Leipertz et al. | |
| 8,218,147 B2 | 7/2012 | Janssen et al. | |
| 8,223,337 B2 | 7/2012 | Janssen et al. | |
| 2002/0154289 A1 | 10/2002 | Wilks, Jr. | |
| 2004/0237505 A1 | 12/2004 | Leipertz | |
| 2005/0076655 A1 | 4/2005 | Wong | |
| 2005/0247066 A1 * | 11/2005 | Myhre | 60/803 |
| 2006/0251548 A1 | 11/2006 | Willey et al. | |
| 2006/0256330 A1 | 11/2006 | Leipertz | |
| 2007/0029487 A1 | 2/2007 | Wong et al. | |
| 2007/0029488 A1 | 2/2007 | Wong | |
| 2007/0068495 A1 * | 3/2007 | Karst | 123/494 |
| 2008/0295499 A1 | 12/2008 | Driscoll | |
| 2009/0193794 A1 | 8/2009 | Robel | |
| 2010/0083636 A1 | 4/2010 | Wang | |
| 2010/0101213 A1 | 4/2010 | Tuomivaara | |

* cited by examiner

OPTICAL SENSING IN AN ADVERSE ENVIRONMENT

The present application is a continuation of U.S. patent application Ser. No. 12/818,817 filed on Jun. 18, 2010, now abandoned, which is a continuation of U.S. patent application Ser. No. 12/610,800 filed on Nov. 2, 2009, now abandoned, which claims the benefit of U.S. Provisional Patent Application No. 61/197,898 filed Oct. 31, 2008, each of which is incorporated herein by reference.

RELATED APPLICATIONS

This application is related to, and claims the benefit of, U.S. Provisional Application No. 61/197,898 entitled Optical sensing in an adverse environment and filed on Oct. 31, 2008, which is incorporated herein by reference.

BACKGROUND

Reliably monitoring the combustion process inside an internal combustion engine presents several challenges. Frequently, engine environments operate at very high temperatures that preclude use of many standard sensor types. Further, engine combustion constituents typically include soot and unburned hydrocarbons that can hamper operation of various sensing technologies. Thus, there is an ongoing demand for further contributions in this area.

SUMMARY

One embodiment of the present application is a unique optical sensing technique. Other embodiments including unique devices, apparatus, systems, and methods to remove debris that accumulates on an optical sensing window in an adverse environment. Further embodiments, forms, objects, features, advantages, aspects, and benefits shall become apparent from the following description and drawings.

DESCRIPTION OF THE ILLUSTRATIVE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated embodiments, and any further applications of the principles of the invention as illustrated therein as would normally occur to one skilled in the art to which the invention relates are contemplated and protected.

Figure 1:
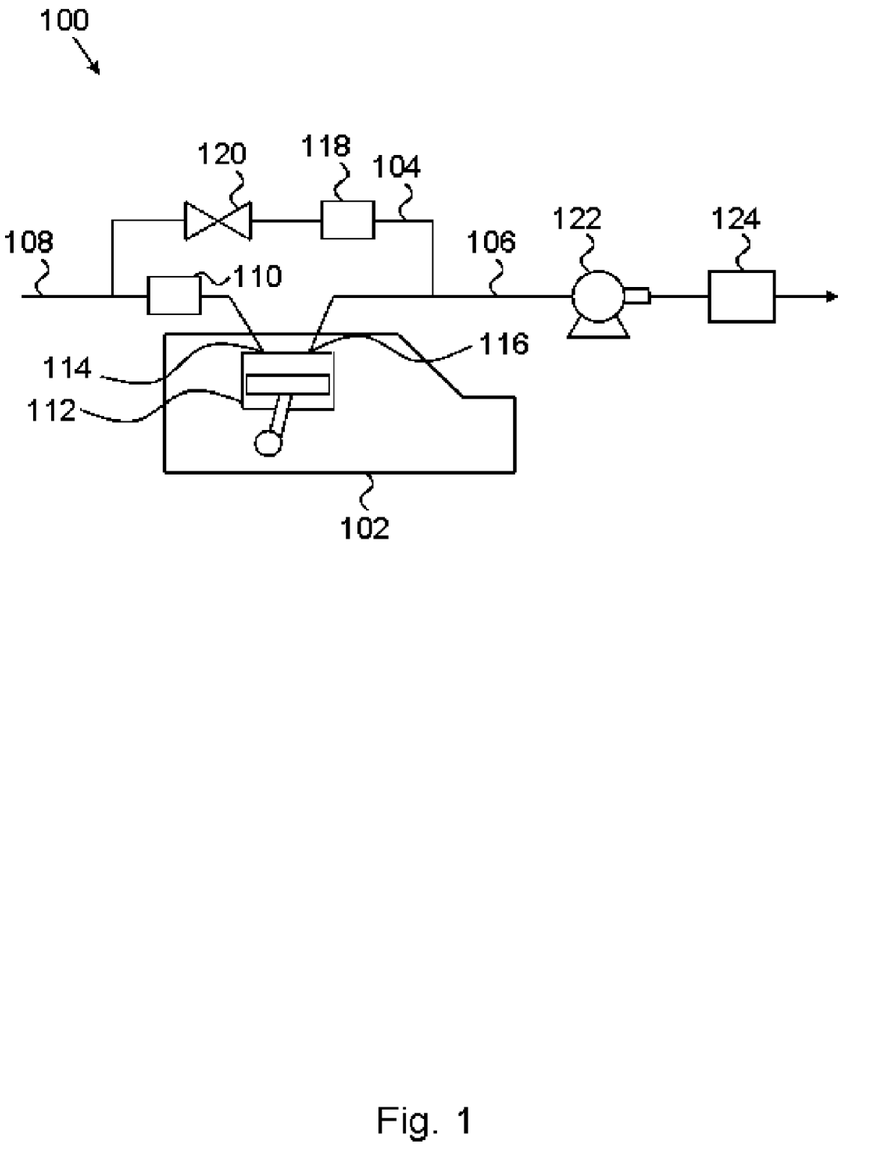
FIG. 1 is a schematic illustration of a system for optical sensing in an adverse environment.

FIG. 1 is a schematic illustration of a system 100 for optical sensing in an adverse environment. In certain embodiments, an optical sensor detects constituents of an engine related gas using electromagnetic (EM) methods such as detecting absorption, detecting phase-shifting, and/or detecting luminescence. The detected constituents include any constituent of interest of an engine working fluid, including without limitation—carbon dioxide, carbon monoxide, unburned hydrocarbons, oxides of nitrogen, oxygen, nitrogen, brass, iron, aluminum, ammonia, and/or urea. Certain features of the optical sensing are not illustrated herein as they are known to those of skill in the art and may obscure aspects of the present application. Adverse environment herein refers to an environment that includes buildup of debris tending to block a window providing optical access to an engine fluid path of interest, and may further refer to high temperatures and the presence of compounds that provide challenges to optical sensing such as soot, unburned hydrocarbons, sulfates, and precipitates from reductants such as urea, ammonia, hydrocarbons, or other reductants known in the art.

Figure 2:
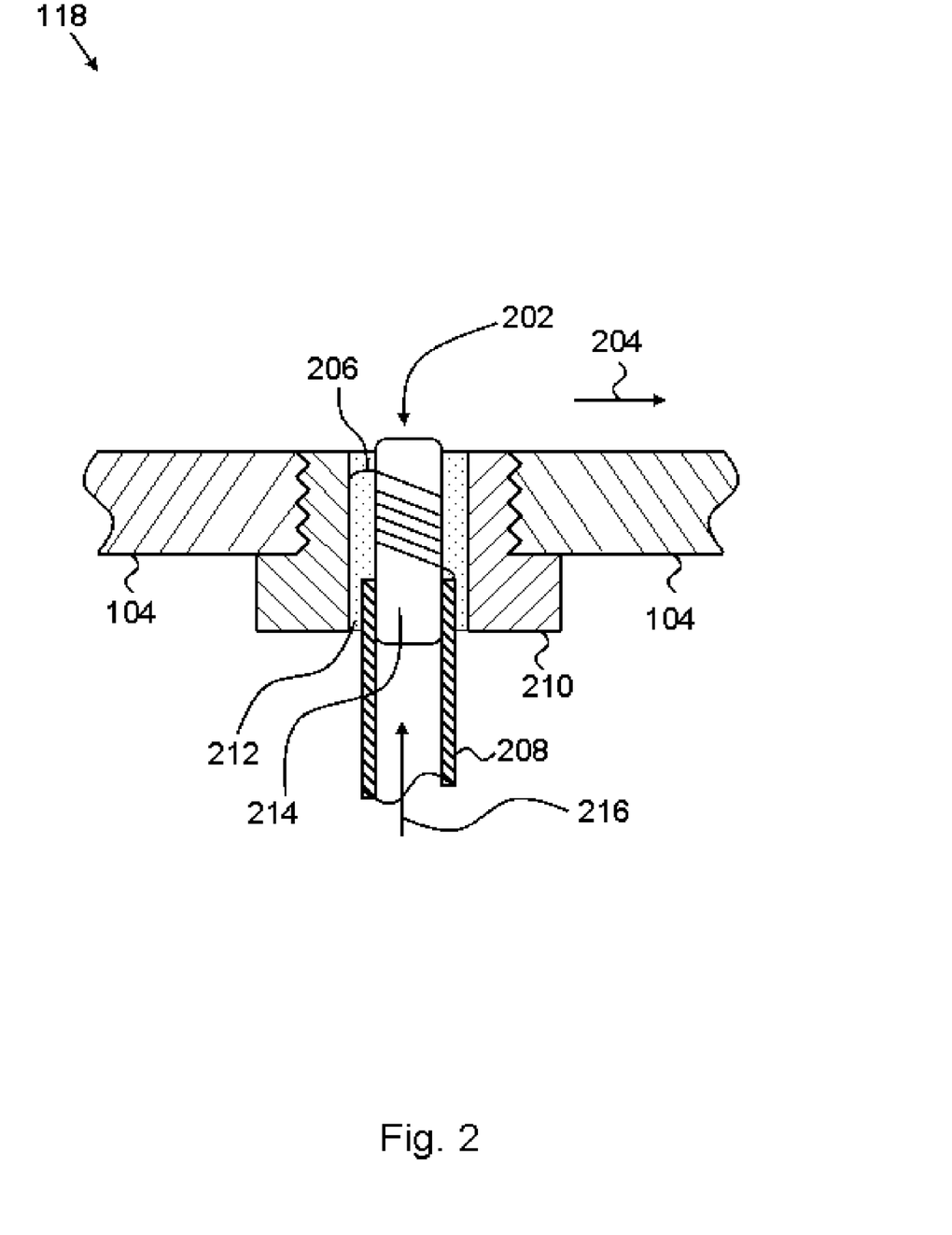
FIG. 2 is a schematic illustration of an optical element cleaning device.

In certain embodiments, the system 100 includes an internal combustion engine 102 having an engine fluid conduit having exhaust combustion byproduct gases therein. In certain embodiments, the system 100 includes an air intake 108, an exhaust gas recirculation valve 120, a turbocharger 122, and an aftertreatment component 124. The engine fluid conduit may be an intake port 114 for a cylinder, an exhaust port 116 for a cylinder, an individual cylinder combustion chamber 112, an exhaust gas recirculation loop 104, an exhaust conduit 106, an intake manifold 110, or an exhaust manifold (not shown). In certain embodiments, the system 100 includes an optical sensor 118 engaged with the engine fluid conduit having an optical element with an exposed face to the engine fluid conduit. Refer to FIG. 2 detailing an embodiment of an optical sensor 118 having a cleaning device for the optical element.

FIG. 2 is a schematic illustration of a portion of an optical sensor 118 engaged with an engine fluid conduit 104. The engine fluid conduit 104 in the illustration of FIG. 2 is an EGR fluid conduit, but any conduit related to the engine including gases that have combustion byproducts may be utilized. The sensor 118 includes an optical element 214 having an exposed face 202 to an engine fluid conduit 104 having combustion byproduct gases 204 flowing therein. The sensor 118 further includes an electrically resistive wire 206 thermally coupled to the optical element 214 such that the electrically resistive wire 206, when heated, heats the exposed face 202 sufficiently to remove accumulated debris. The accumulated debris includes soot, unburned hydrocarbons, sulfates, and/or a reductant precipitate. The temperature required to remove the accumulated debris depends upon the nature of the debris, the content of the combustion byproduct gases 204 (e.g. the oxygen fraction of the gases at the time of heating), the flow rate of the combustion byproduct gases 204, and other factors known in the art. In certain embodiments, heating the exposed face 202 above 400° C. is sufficient to remove debris. In certain embodiments, the temperature required may be 500° C., or greater. The achieved temperature during heating of the electrically resistive wire 206 depends upon the energy transferred from the wire to the optical element, the heat losses from the optical element, the temperature and flow rate of the combustion byproduct gas 204, the thermal conductivity of the optical element 202 and other factors known in the art. In most embodiments involving soot and unburned hydrocarbons as the accumulated debris, heating the wire to a temperature greater than about 600° C. is sufficient for debris removal.

In certain embodiments, the electrically resistive wire 206 includes nickel or a nickel alloy. The resistive wire may be made of any material that sufficiently withstands the temperature and corrosion environment of the system 100 at the optical sensor 118. In certain embodiments, the optical element 214 is sapphire, diamond, or glass. Diamond is known to oxidize in the presence of oxygen at very high temperatures, so testing of the optical element 214 in such applications is recommended if diamond is considered for the optical element 214.

In certain embodiments, the electrically resistive wire 206 is part of an electrical circuit, where the electrical circuit includes a casing 210 for an optical sensor 118, where the casing 210 defines the optical element 214, and a metal tube 208 that conveys electromagnetic (EM) radiation 216 to the optical element 214 from an EM source (not shown).

For example, a voltage source (not shown) may apply power to the metal tube 208 and ground through the casing 210, or the voltage source may apply power to the casing 210 and ground through the metal tube 208. In certain embodiments, the electrically resistive wire 206 may be part of a circuit that does not include the casing 210 and/or the metal tube 208, or the electrically resistive wire 206 may have a dedicated circuit.

In certain embodiments, an opposing optical element (not shown) across the engine fluid conduit 104 has a similar sealing and resistive wire configuration, with an optical conduit (that may be a metal tube) leading to an EM detection device (not shown). In certain embodiments, the opposing optical element may be a mirror having a resistive wire heater that allows cleaning of the mirror, and the metal tube 208 also conveys returning EM radiation to an EM detector. Certain details of a sensing device, as described in pending patent application entitled "APPARATUS, SYSTEM, AND METHOD FOR DETECTING ENGINE FLUID CONSTITUENTS", assigned to the assignee of the present application and incorporated herein by reference in the entirety, may be useful in understanding the present application.

In certain embodiments, the exposed face 202 cooperates with casing 210 to seal the optical sensor 118 from the engine fluid conduit 104. In certain embodiments, the exposed face 202 further cooperates with the casing 210 and a filler material 212 to seal the optical sensor 118 from the engine fluid conduit 104. In certain further embodiments, the filler material 212 is mineral wool and/or ceramic filler such as ceramic fibers. The seal of the optical sensor 118 does not need to be a perfect seal, but in certain embodiments the sensor 118 is sufficiently sealed that combustion byproduct gases 204 do not enter the metal tube 208 and impede passing of EM radiation 216.

The filler material 212 may be any material that provides sufficient thermal and corrosion resistance, that contributes to the seal of the sensor 118, and that is amenable to sufficient bonding mechanisms with the optical element 202, the casing 206, and/or the tubing 208. In certain embodiments, the filler material electrically isolates the resistive wire 206 from the casing 210 except at a point of intentional contact—for example at a spot weld creating intentional electrical contact between the resistive wire 206 and the casing 210.

Figure 3:
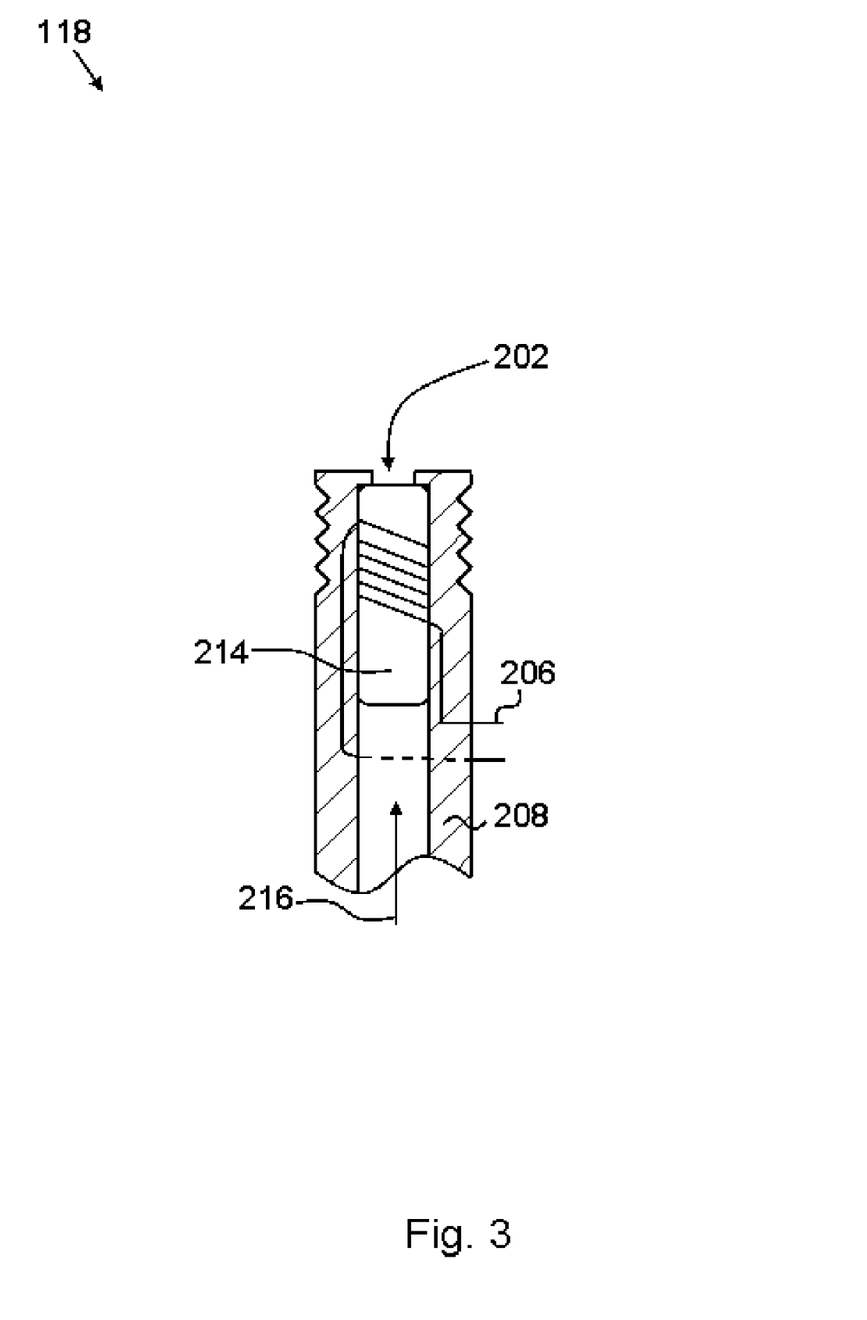
FIG. 3 is an alternate schematic illustration of an optical element cleaning device.

FIG. 3 is an alternate schematic illustration of an optical element cleaning device. In the illustration of FIG. 3, the exposed face 202 cooperates with the metal tube 208 to seal the optical sensor 118 from the engine fluid conduit 104, wherein the metal tube 208 conveys electromagnetic (EM) radiation 216 to the optical element 214 from an EM source (not shown) to seal the optical sensor 118 from the engine fluid conduit 104. In the illustration of FIG. 3, the resistive wire 206 is shown with a dedicated circuit to a voltage provider (not shown) rather than routing power through other portions of the sensor 118 such as the metal tube 208.

Figure 4:
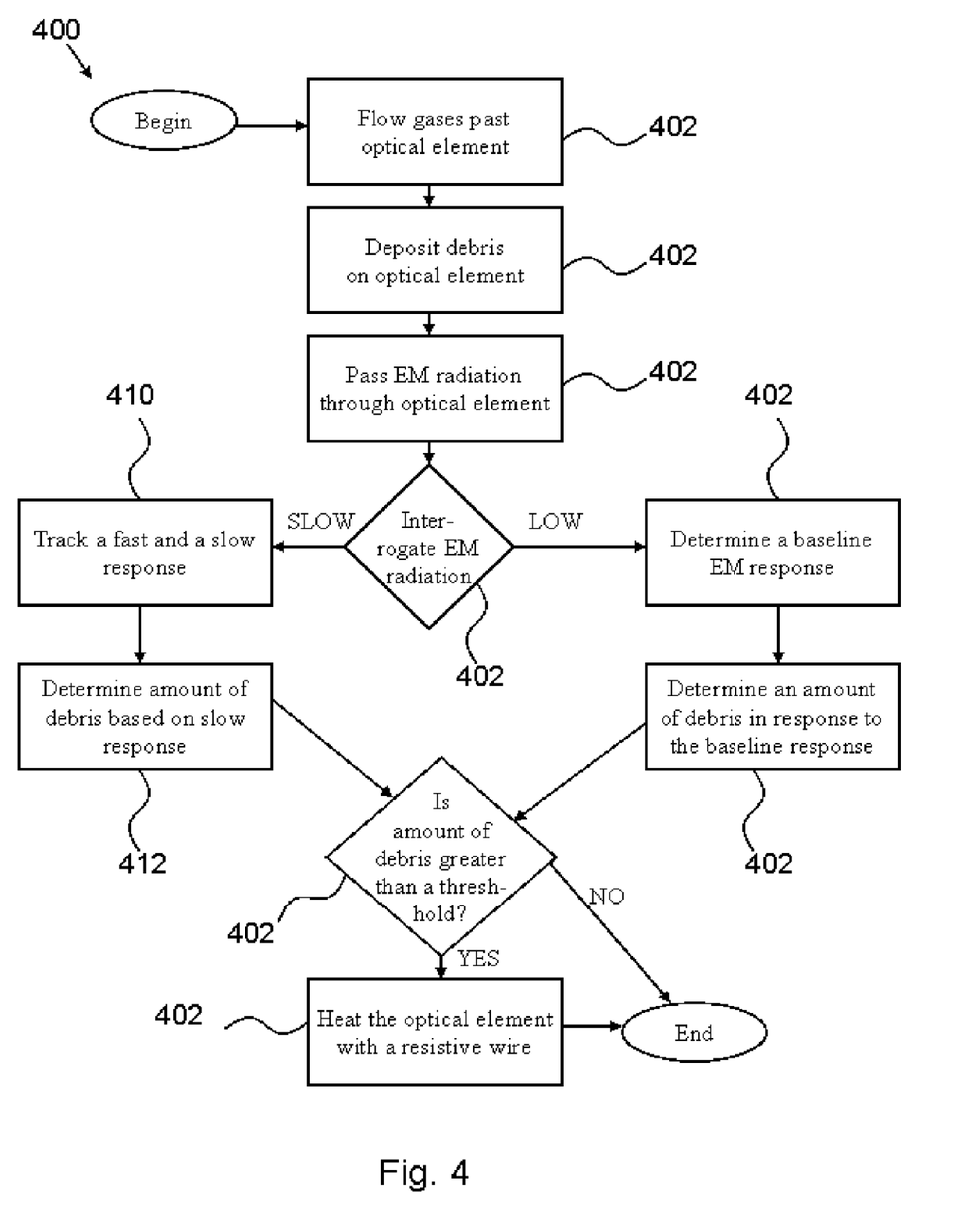
FIG. 4 is a schematic flow diagram of a procedure to clean an optical element.

The schematic flow diagram FIG. 4 and related description which follows provides an illustrative embodiment of operations related to the present application. Operations shown are understood to be illustrative only, and operations may be combined or divided, and added or removed, as well as re-ordered in whole or part, unless stated explicitly to the contrary herein.

FIG. 4 is a schematic flow diagram of a procedure 400 to clean an optical element. The procedure 400 includes an operation 402 to flow gases including combustion byproducts past an exposed face of an optical element in an engine fluid conduit. The procedure further includes an operation 404 to deposit debris on the exposed face of the optical element, where the debris is soot, unburned hydrocarbons, sulfates, and/or a reductant precipitate. In certain embodiments, the procedure 400 further includes an operation 406 to pass electromagnetic (EM) radiation through the optical element and the flowing gases, and an operation to determine interrogate the EM radiation after passing through the optical element and the flowing gases to determine an amount of debris accumulated on the exposed face of the optical element. In certain embodiments, the EM radiation is selected at a wavelength that is responsive to soot and/or debris, but that is not responsive to other constituents in the flowing gas 204.

In certain embodiments, the operation to interrogate the EM radiation includes an operation 408 to determine an interrogation method which may be tracking a low response value or tracking a slow response value and a fast response value. In response to the interrogation method including tracking a slow response value and a fast response value, the procedure 400 includes an operation 410 to track a fast response and a slow response value. The slow response value is a heavily filtered (i.e. large time constant, for example greater than 10 seconds, 30 seconds, or a minute), and may be filtered such that the value rises slowly (larger time constant) and falls quickly (smaller time constant). The fast response value is lightly filtered (i.e. small time constant such as less than 30 seconds, 10 seconds, or even 1 second) or unfiltered (i.e. raw sensed value is utilized, or only a diagnostically filtered value to remove noise). The procedure 400 further includes an operation 412 to determine an amount of debris based on the slow response, and may further include an operation to determine an amount of soot based on the fast response value (presumably representing the soot plus debris) minus the slow response value (presumably representing the debris only).

In response to the interrogation method including tracking a low value, the procedure 400 includes an operation 414 to determine a baseline EM response. For example, the operation 414 may track a lowest observed value of the EM response over a recent time period (e.g. the last five minutes) or during a recent low-soot event (e.g. during an engine motoring event). The lowest recent observation may be due to debris primarily and represent the non-soot portion of the response.

The procedure 400 further includes, in certain embodiments, an operation 418 to determine whether an amount of debris is greater than a threshold. The threshold amount may be defined by an acceptable loss amount of the EM radiation passing through the optical element(s) 214. For example, as the debris value rises and the EM radiation received after passing through the engine fluid conduit 104 falls, the signal to noise ratio of the optical sensor 118 may rise to an unacceptable level, or the EM radiation may be lost altogether. In response to the amount of debris being greater than the threshold, the procedure 400 includes an operation 420 to heat the optical element with a resistive wire. The time and temperature of heating may be as defined according to predetermined values, may depend upon the initial amount of debris, and/or may continue until the amount of debris falls below a second threshold. The second threshold to stop heating is, in certain embodiments, lower than the threshold to begin cleaning to prevent cycling of the operation 420 to heat the optical element.

As is evident from the figures and text presented above, a variety of embodiments according to the present invention are contemplated.

One exemplary embodiment is an apparatus including an optical element having an exposed face to an engine fluid conduit having combustion byproduct gases therein, and a resistive wire thermally coupled to the optical element such that the resistive wire, when heated, heats the exposed face sufficiently to remove accumulated debris. The accumulated debris includes soot, unburned hydrocarbons, sulfates, and/or a reductant precipitate. In certain embodiments, the resistive wire includes nickel or a nickel alloy. In certain embodiments, the resistive wire is part of an electrical circuit, where the electrical circuit includes a casing for an optical sensor defining the optical element, and a metal tube that conveys electromagnetic (EM) radiation to the optical element from an EM source. In certain embodiments, the exposed face cooperates with the casing to seal the optical sensor from the engine fluid conduit. In certain embodiments, the exposed face cooperates with the casing and a filler material to seal the optical sensor from the engine fluid conduit. In certain further embodiments, the filler material is mineral wool and/or ceramic filler. In certain embodiments, the filler material electrically isolates the resistive wire from the casing except at a point of intentional contact. In certain embodiments, the exposed face cooperates with a metal tube to seal the optical sensor from the engine fluid conduit, wherein the metal tube conveys electromagnetic (EM) radiation to the optical element from an EM source to seal the optical sensor from the engine fluid conduit.

One exemplary embodiment is a method including flowing gases including combustion byproducts past an exposed face of an optical element in an engine fluid conduit, depositing debris on the exposed face of the optical element, where the debris is soot, unburned hydrocarbons, sulfates, and/or a reductant precipitate, and the method includes heating a resistive wire thermally coupled to the optical element sufficiently to remove accumulated debris from the exposed face. In certain embodiments, the method further includes performing the heating periodically. In certain embodiments, the method further includes optically detecting an amount of accumulated debris, and performing the heating in response to determining the amount of accumulated debris is greater than a threshold. In certain embodiments, the method further includes providing an electrical circuit comprising a metal tube conveying electromagnetic (EM) radiation to the optical element, the resistive wire, and a casing for an optical sensor defining the optical element.

One exemplary embodiment is a method including flowing gases including combustion byproducts past an exposed face of an optical element in an engine fluid conduit, depositing debris on the exposed face of the optical element, where the debris is soot, unburned hydrocarbons, sulfates, and/or a reductant precipitate. The method further includes passing electromagnetic (EM) radiation through the optical element and the flowing gases, interrogating the EM radiation after passing through the optical element and the flowing gases to determine an amount of debris accumulated on the exposed face of the optical element, and heating a resistive wire thermally coupled to the optical element sufficiently to remove accumulated debris from the exposed face in response to the amount of debris exceeding a threshold. In certain embodiments, the method includes heating the resistive wire in response to an elapsed time since a previous heating event exceeding a time threshold.

In certain embodiments, the EM radiation is responsive to soot and debris and substantially non-responsive to other constituents of the flowing gases, and interrogating the EM radiation includes determining a baseline observed EM radiation response comprising a lowest observed EM radiation response over a recent time period, and determining the amount of debris in response to the baseline observed EM radiation response.

In certain embodiments, the EM radiation is responsive to soot and debris and substantially non-responsive to other constituents of the flowing gases, and interrogating the EM radiation includes tracking a fast observed EM radiation response and a slow observed EM radiation response, and determining the amount of debris according to the slow observed EM radiation response and an amount of soot according to the slow observed EM radiation response subtracted from the fast observed EM radiation response.

One exemplary embodiment is a system including an internal combustion engine having an engine fluid conduit having exhaust combustion byproduct gases therein, an optical element having an exposed face to the engine fluid conduit, a resistive wire thermally coupled to the optical element such that the resistive wire, when heated, heats the exposed face sufficiently to remove accumulated debris, and the accumulated debris is soot, unburned hydrocarbons, sulfates, and/or reductant precipitate. In certain embodiments, the engine fluid conduit is an intake port for a cylinder, an exhaust port for a cylinder, an individual cylinder combustion chamber, an exhaust gas recirculation loop, an exhaust conduit, an intake manifold, or an exhaust manifold. In certain embodiments, the system includes a metal tube that conveys electromagnetic (EM) radiation to the optical element from an EM source. In certain embodiments, the system includes a metal tube that is extruded aluminum, extruded stainless steel, a polished metal, or a machined metal. In certain embodiments, the optical element is sapphire, diamond, or glass.

Another exemplary embodiment is an apparatus including an internal combustion engine. The internal combustion engine includes a sensor responsive to one or more wavelengths of electromagnetic radiation to detect one or more selected constituents of a working fluid in the engine, where the working fluid of the engine includes any fluid stream related to the engine. The apparatus further includes an optical element that transmits the one or more wavelengths of electromagnetic radiation therethrough, where the optical element includes a face in fluid communication with the working fluid. The face of the optical element is susceptible to accumulation of debris that at least partially occludes transmission of the one or more wavelengths therethrough. The apparatus further includes a heating element thermally coupled to the optical element, where the heating element heats the optical element sufficiently to at least partially remove the debris.

Another exemplary embodiment is a method including operating an internal combustion engine that includes passage of a working fluid along a pathway therethrough. The method includes, during the operating of the engine, sensing one or more wavelengths of electromagnetic radiation to detect one or more selected constituents of the working fluid. The method further includes transmitting the one or more wavelengths through an optical window that includes a face exposed to the working fluid, and further during the operating of the engine, the face accumulating debris that at least partially occludes transmission of the one or more wavelengths therethrough. The method further includes heating the optical window to at least partially remove the debris.

In certain further embodiments, the optical window is a sapphire window. The accumulated debris includes at least one debris constituent selected from the debris constituents consisting of: soot, unburned hydrocarbons, sulfates, and reductant precipitate. The heating element includes an electrically resisitive device and/or a wire. The selected constituents include carbon dioxide, carbon monoxide, an oxide of nitrogen, an oxide of sulfur, and/or a gaseous alkane.

While the invention has been illustrated and described in detail in the drawings and foregoing description, the same is to be considered as illustrative and not restrictive in character, it being understood that only certain illustrative embodiments have been shown and described and that all changes and modifications that come within the spirit of the inventions are desired to be protected. It should be understood that any relative characterization of embodiments such as but not limited to preferable, preferably, preferred, more preferred, advantageous, or exemplary utilized in the description above indicate that the embodiments or features thereof so described may be more desirable or characteristic, nonetheless the embodiments or features thereof may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. An apparatus, comprising:
an optical element structured to transmit electromagnetic radiation of one or more selected wavelengths therethrough, the optical element including having an exposed face to an engine fluid conduit having combustion byproduct gases therein;
an electric heating element thermally coupled to the optical element, wherein the electric heating element is structured to heat the optical element sufficiently to remove accumulated debris;
wherein the accumulated debris comprises at least one member from the group consisting of: soot, unburned hydrocarbons, sulfates, and reductant precipitate; and
wherein the exposed face cooperates with a metal tube to seal an optical sensor defining the optical element from the engine fluid conduit, wherein electromagnetic (EM) radiation is conveyed by the metal tube to the optical element from an EM source.

2. The apparatus of claim 1, wherein the electric heating element comprises one of nickel and a nickel alloy.

3. The apparatus of claim 1, wherein the electric heating element comprises a portion of an electrical circuit, the electrical circuit including the metal tube and a casing for the optical element, the casing containing a filler material around the optical element to seal the metal tube from the engine fluid conduit, wherein the electric heating element extends through the filler material and electrically connects the metal tube to the casing.

4. The apparatus of claim 1, wherein the electric heating element comprises an electrically resistive wire.

5. The apparatus of claim 1, further comprising a means for removing accumulated debris from the optical element.

6. The apparatus of claim 3, wherein the filler material comprises one of mineral wool and ceramic filler.

7. The apparatus of claim 3, wherein the filler material electrically isolates the electric heating element from the casing except at a point of intentional contact.

8. A system, comprising:
an internal combustion engine having an engine fluid conduit having exhaust combustion byproduct gases therein;
an optical element having an exposed face to the engine fluid conduit;
a resistive wire thermally coupled to the optical element such that the resistive wire, when heated, heats the exposed face sufficiently to remove accumulated debris;
wherein the accumulated debris comprises at least one member from the group consisting of: soot, unburned hydrocarbons, sulfates, and reductant precipitate; and
wherein the exposed face cooperates with a metal tube to seal an optical sensor defining the optical element from the engine fluid conduit, and wherein electromagnetic (EM) radiation is conveyed by the metal tube to the optical element from an EM source.

9. The system of claim 8, wherein the engine fluid conduit comprises a conduit selected from the group consisting of an intake port for a cylinder, an exhaust port for a cylinder, an individual cylinder combustion chamber, an exhaust gas recirculation loop, an exhaust conduit, an intake manifold, and an exhaust manifold.

10. The system of claim 8, wherein the metal tube comprises at least one metal selected from the metals consisting of extruded aluminum, extruded stainless steel, a polished metal, and a machined metal.

11. The system of claim 8, wherein the optical element comprises a material selected from the materials consisting of sapphire, diamond, and glass.

12. The apparatus of claim 8, wherein the resistive wire comprises a portion of an electrical circuit, the electrical circuit including the metal tube and a casing for the optical element, the casing containing a filler material around the optical element to seal the metal tube from the engine fluid conduit, wherein the resistive wire extends through the filler material and electrically connects the metal tube to the casing.

13. An apparatus, comprising:
an internal combustion engine including:
a sensor responsive to one or more wavelengths of electromagnetic radiation to detect one or more selected constituents of a working fluid in the engine;
an optical element structured to transmit the one or more wavelengths of electromagnetic radiation therethrough, the optical element including a face in fluid communication with the working fluid, the face being susceptible to accumulation of debris that at least partially occludes transmission of the one or more wavelengths therethrough;
a heating element thermally coupled to the optical element, the heating element being structured to heat the optical element sufficiently to at least partially remove the debris; and
wherein the face in fluid communication with the working fluid cooperates with a metal tube to seal an optical sensor defining the optical element from the working fluid, and wherein electromagnetic (EM) radiation is conveyed by the metal tube to the optical element from an EM source.

14. The apparatus of claim 13, wherein the debris includes at least one debris constituent selected from the debris constituents consisting of: soot, unburned hydrocarbons, sulfates, and reductant precipitate.

15. The apparatus of claim 13, wherein the heating element is an electrically resistive device.

16. The apparatus of claim 13, wherein the optical element includes sapphire.

17. The apparatus of claim 13, wherein the one or more selected constituents include at least one constituent selected from the constituents consisting of: carbon dioxide, carbon monoxide, an oxide of nitrogen, an oxide of sulfur, and a gaseous alkane.

18. The apparatus of claim 13, wherein the heating element comprises a portion of an electrical circuit, the electrical circuit including the metal tube and a casing for the optical element, the casing containing a filler material around the optical element to seal the metal tube from the working fluid, wherein the electric heating element extends through the filler material and electrically connects the metal tube to the casing.

19. The apparatus of claim 15, wherein the device includes a wire.

* * * * *